US008784322B2

(12) United States Patent
Kim et al.

(10) Patent No.: US 8,784,322 B2
(45) Date of Patent: Jul. 22, 2014

(54) APPARATUS AND METHOD OF SENSING SLEEPING CONDITION OF USER

(75) Inventors: Jong Pal Kim, Seoul (KR); Kun Soo Shin, Seongnam-si (KR); Soo Hyun Bae, Seoul (KR); Mi Hee Lee, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1245 days.

(21) Appl. No.: 11/812,526

(22) Filed: Jun. 19, 2007

(65) Prior Publication Data
US 2008/0009685 A1 Jan. 10, 2008

(30) Foreign Application Priority Data
Jun. 20, 2006 (KR) .................. 10-2006-0055603

(51) Int. Cl.
*A61B 5/02* (2006.01)
(52) U.S. Cl.
USPC ........................................... 600/481; 600/509
(58) Field of Classification Search
USPC ......... 600/481, 528–529, 538, 532–534, 509; 364/413.01, 413.02, 413.03, 413.05, 364/413.06
See application file for complete search history.

(56) References Cited

U.S. PATENT DOCUMENTS

| 4,922,930 | A | * | 5/1990 | Adkins et al. ................. 607/19 |
| 4,999,772 | A | | 3/1991 | Bowman et al. |
| 5,047,930 | A | * | 9/1991 | Martens et al. ............... 600/301 |
| 5,197,489 | A | * | 3/1993 | Conlan ......................... 600/595 |
| 5,280,791 | A | * | 1/1994 | Lavie ............................ 600/509 |
| 5,427,112 | A | * | 6/1995 | Noren et al. ................... 600/515 |
| 5,704,365 | A | * | 1/1998 | Albrecht et al. .............. 600/515 |
| 6,047,203 | A | * | 4/2000 | Sackner et al. ............... 600/388 |
| 7,640,055 | B2 | * | 12/2009 | Geva et al. .................... 600/544 |
| 2003/0004423 | A1 | | 1/2003 | Lavie et al. |
| 2003/0163059 | A1 | | 8/2003 | Poezevera et al. |
| 2004/0073098 | A1 | | 4/2004 | Geva et al. |
| 2004/0225199 | A1 | * | 11/2004 | Evanyk et al. ................ 600/300 |
| 2005/0119586 | A1 | * | 6/2005 | Coyle et al. .................. 600/538 |
| 2005/0267362 | A1 | | 12/2005 | Mietus et al. |
| 2007/0293731 | A1 | * | 12/2007 | Downs et al. ................. 600/300 |

FOREIGN PATENT DOCUMENTS

| JP | 08-112270 | 5/1996 |
| JP | 2001-231864 | 8/2001 |
| KR | 2005-72435 | 7/2005 |

OTHER PUBLICATIONS

"Sleep-Wake Identification in Infants: Heart Rate Variability Compared to Actigraphy" by Lewicke et al., IEEE EMBS, pp. 442-445, 2004.*

* cited by examiner

*Primary Examiner* — Charles A Marmor, II
*Assistant Examiner* — Vasuda Ramachandran
(74) *Attorney, Agent, or Firm* — Staas & Halsey LLP (57) ABSTRACT

A method and apparatus for sensing a sleeping condition of a user, including measuring a physiological signal of a user who is sleeping, determining whether or not a predetermined motion artifact is contained in the measured physiological signal, and determining that the user goes into an awake state when the predetermined motion artifact is contained in the measured physiological signal.

26 Claims, 10 Drawing Sheets

APPARATUS AND METHOD OF SENSING SLEEPING CONDITION OF USER

CROSS-REFERENCE TO RELATED APPLICATIONS

This application claims priority from Korean Patent Application No. 10-2006-0055603, filed on Jun. 20, 2006, in the Korean Intellectual Property Office, the disclosure of which is incorporated herein by reference.

BACKGROUND

1. Field

The present invention relates to an apparatus and method of sensing a sleeping condition of a user, and more particularly, to a sleeping condition-sensing apparatus and method in which it is determined that a user who is sleeping moves into an awake state when his or her physiological signal is measured and a certain motion artifact is sensed from the measured physiological signal.

2. Description of the Related Art

Sleep provides human beings with essential resting time for relaxation and it is through sleep that the supply of energy is carried out to reserve physical power. Sleep is the time period during which human beings supplement energy consumed while doing activities during the day time. Further, human growth hormone (HGH) indispensable for children in a growth phase is secreted in the greatest amount just during the sleep period. The brain of our body is a complex organ that collectively controls all the physiological functions for sustaining the human life and physical rest is necessary for the brain to maintain a suitable balance of its activities. This bodily rest is primarily taken during the sleep period.

As such, although one cannot emphasize too much the importance of sleep, most modern people do not sleep sufficiently due to excessive loads of business, schoolwork or the like. Most important in sleep is the quality of sleep, rather than the quantity of sleep. Particularly, whether or not people take a deep sleep is significantly crucial, however almost all modern people do not maintain a good quality of sleep at night.

In order to get a good quality of sleep for the rest at night, it is required that after an individual person has determines the quality of his or her sleep, he or she should seek measures to cope with its result. There are many occasions where all people do not exactly recognize the quality of their sleeps in their real lives as in the case where a person does not feel refreshed but is still tired despite a long sleep, i.e., in the case where the person feels the person sleeps well but is easily tired, or in the case where the person thinks the person tossed and turned all night long but actually has no problem with the person's sleep itself, etc. This falls within a kind of problem that can be accurately identified only when the ordinary sleeping condition of an individual is measured and digitized by means of an objective measurement instrument. Even when there is no case of such a distinct problem, the optimum sleep time for each individual will be able to be derived by digitizing the quality of his or her sleep. There is a need for development of a simple measurement instrument to determine the quality of an individual's sleep. But, up to now, polysomnography (PSG), which is performed in a sleep lab of a hospital, is a unique objective method of diagnosing and quantifying the quality of sleep or the severity of sleep disordered breathing (SDB).

Figure 1:
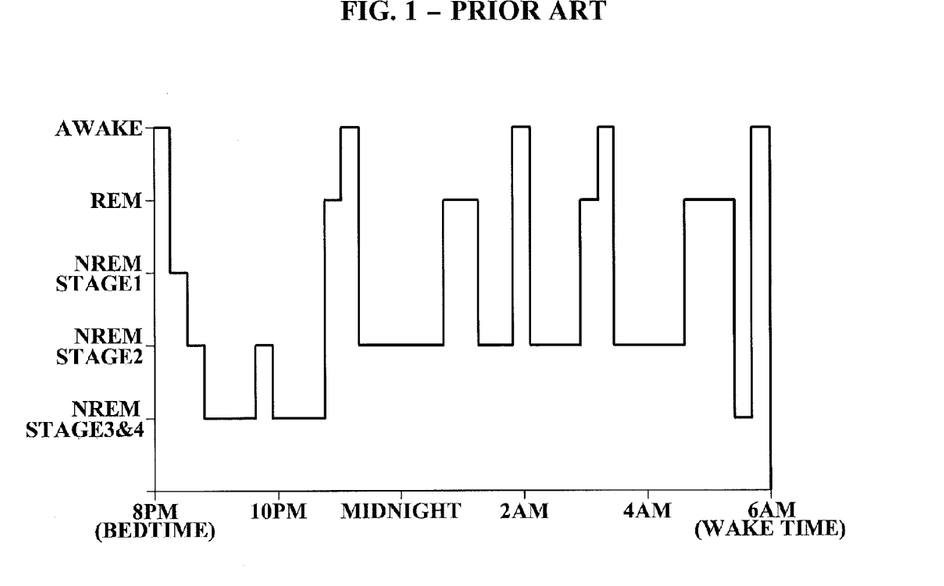
FIG. 1 is a graph illustrating the period of respective human sleep stages classified based on polysomnography (PSG)

A human sleep classified based on the PSG is described as a succession of five recurring stages including four non-rapid eye movement (NREM) stages and a rapid eye movement (REM) stage. During a normal sleep period at night, a person usually periodically goes through a sequential sleep cycle of stage 1, 2, 3, 4, 3, 2 and REM in a period of approximately 90 minutes. The sequence of such a sleep cycle is shown in FIG. 1.

The determination of a subject's sleeping condition is performed by an expert who has integrated various measuring signals obtained from PSG while he or she sleeps in a hospital lab at night. Sleeping condition, obstructive sleep apnea (OSA), arrhythmia, rapid eye movement, etc., are diagnosed and evaluated by synthesizing various kinds of signals. The quality of sleep is determined depending on how a subject is frequently awakened from sleep or frequently moves into deep-sleep stages 3 and 4 during the sleep period.

The signals measured during PSG includes signals associated with electroencephalogram (EEG), electro-oculogram (EOG), electromyogram (EMG), electrocardiogram (ECG), arterial oxygen saturation ($SaO_2$), chest and abdomen respiratory effect, nasal airflow, snoring, body temperature, body position changes and recorded video for identifying the subject's tossing and turning during sleep, and the like. Since these various special instruments must be used for PSG, the subject suffers from an inconvenience of having to sleep in a sleep lab of a hospital and the cost for polysomnography is increased. In addition, PSG requires transformation of a sleeping environment into a hospital sleep lab, but not a place where a person usually sleeps so that a sleeping subject may exhibit a different characteristic of sleeping condition than that of ordinary times. Furthermore, a variety of measurement instruments are respectively attached to head, eye peripheries, chin peripheries, chest, abdominal region, etc., of a sleeping subject for the purpose of measurement of various signals, so that inconvenience and displeasure are is given to him or her, and he or she also shows a different characteristic of sleeping condition than that of ordinary times, making it difficult to diagnose this sleeping condition as a normal one.

Therefore, efforts are required to reduce the number of measurement instruments to be attached to a sleeping subject to increase convenience of use, to build a sleeping environment more similar to an ordinary one and with reduced costs, and to limit an attaching position of the measurement instruments to bodily regions excluding the head or face. Research is being conducted on diagnosis of sleeping condition using only an ECG signal as part of these efforts. In this case, ECG signals are processed based on heart rate variability (HRV) so as to extract low-frequency components and high-frequency components from the signals to thereby determine an awake stage, stages 1, 2, 3, 4 and REM. However, in the case of the HRV-based sleeping condition diagnosis, a degree of dispersion is increased and hence a differentiation between respective sleep stages is impossible.

When only awake stages and the remaining sleep stages are differentiated without accurately distinguishing all the awake stages, stages 1, 2, 3, 4 and REM from one another, the quality of sleep can be assessed. The frequency of awakenings during the PSG test is used as an index for determining the quality of a subject's sleep. As shown in FIG. 1, sufficient time is spent to go into deep-sleep stages 3 and 4. In this case, recurrent awakenings from sleep means a state where a subject did not fall into deep-sleep phases as often, and the period of stages 3 and 4 and the frequency of awakenings are inversely proportional to each other.

A conventional prior technique for assessing the quality of sleep employs electrical measurement, optical measurement, ECG, galvanic skin response (GSR), etc. In the case of the electrical measurement method, a motion artifact is generated due to electrodes themselves attached to a skin in the region of a soft body tissue and a skin tissue epidermis and a change in the electric properties (e.g., impedance) between the electrodes by a subject's movement. Also, in the case of the optical measurement method, a motion artifact is generated due to a skin tissue itself and a change in the optical properties between the skin tissue and a light source by a subject's bodily motion. In addition, in the case of the ECG or GSR method, when a physiological signal of a subject is measured, a myo-electric signal generated due to his or her bodily motion also falls within a kind of motion artifact. Such a motion artifact is regarded as a noise signal and becomes a target to be eliminated in the case of measuring a physiological signal of a sleeping subject for the purpose of assessment of the quality of his or her sleep. Then, in order to sense the subject' being tossed and turned during the sleep, a method of recording his or her images using a camera to diagnose the quality of sleep, and a method of attaching a separate motion sensor such as an accelerometer to the sleeping subject to identify his or her motion.

However, in assessment of the quality of sleep, REM stage sleep is important, but the frequency of awakenings during the sleep is an insignificant factor. Therefore, there is an urgent need for an apparatus for and method of sensing a sleeping condition in which the quality of sleep can be more easily and simply determined based on a motion artifact signal without an additional measurement instrument.

SUMMARY

Additional aspects and/or advantages will be set forth in part in the description which follows and, in part, will be apparent from the description, or may be learned by practice of the invention.

An aspect of the present invention to provide an apparatus for and method of sensing a sleeping condition of a user in which it is determined that a sleeping user moves into an awake state when a certain motion artifact is sensed from his or her physiological signal being measured, so that the quality of sleep can be determined based on only a motion artifact signal generated during the measurement of the physiological signal of the user without an additional physiological signal measuring instrument.

Another aspect of the present invention is to provide an apparatus for and method of sensing a sleeping condition of a user in which a sleeping user's falling into an awake stage is sensed and predicted through a motion artifact generated from a physiological signal of the user so as to provide an alarm to him or her within an alarm time range preset by the user so that he or she can optimize the time to get up, i.e., an awake time.

To accomplish the above aspects, according to one aspect of the present invention, there is provided a method of sensing a sleeping condition of a user, the method including: measuring a physiological signal of a user who is sleeping; determining whether or not a predetermined motion artifact is contained in the measured physiological signal; and determining that the user goes into an awake state when the predetermined motion artifact is contained in the measured physiological signal.

BRIEF DESCRIPTION OF THE DRAWINGS

The above and other aspects, features and advantages of the present invention will be apparent from the following detailed description of the preferred embodiments of the invention in conjunction with the accompanying drawings, in which.

DETAILED DESCRIPTION OF THE EMBODIMENTS

Reference will now be made in detail to embodiments of the present invention, examples of which are illustrated in the accompanying drawings, wherein like reference numerals refer to the like elements throughout. The embodiments are described below in order to explain the present invention by referring to the figures.

As used herein, the term "a physiological signal" means a signal including an electrocardiogram (ECG) signal, a photoplethysmogram (PPG) signal, or a galvanic skin response (GSR) signal. Also, the physiological signal may be implemented with an electroencephalogram (EEG) signal, an electro-oculogram (EOG) signal or an electromyogram (EMG) signal.

The physiological signal may include various kinds of signals widely used in the art for the purpose of measurement of sleep stages besides these signals. Herein, for the sake of convenience of explanation, there will be hereinafter described an example of the case where sleep stages are determined by measuring the ECG signal among the above-mentioned physiological signals, i.e., ECG of a user who is sleeping.

ECG can be represented by a graph of electrical activity of the heart obtained by inducing excitation of a myocardium, which occurs from a vinus venosus and proceeds toward an atria and a ventricle, to an electrocardiograph at two arbitrary points of the human body. This ECG can be utilized as very critical data for diagnosis of cardiac disorder as well as coronary artery diseases such as angina pectoris, cardiac infarction or the like, and various arrhythmia or electrolyte disorder, or identification of whether or not there is a symptom of cardiac disorder during the operation.

The apparatus for sensing a sleeping condition according to the present invention can adopt an ECG measuring method based on a standard limb lead including a first lead of the ECG from both hands, a second lead of the ECG from the right hand and the left foot, and a third lead of the ECG from the left hand and the left foot. Besides this standard limb lead-based method, it is possible to apply an electrocardiogram measuring method based on a unipolar lead or a precordial lead as well as an electrocardiogram measuring method which can be typically performed.

An embodiment of the present invention will be described hereinafter in detail with reference to the accompanying drawings.

Figure 2:
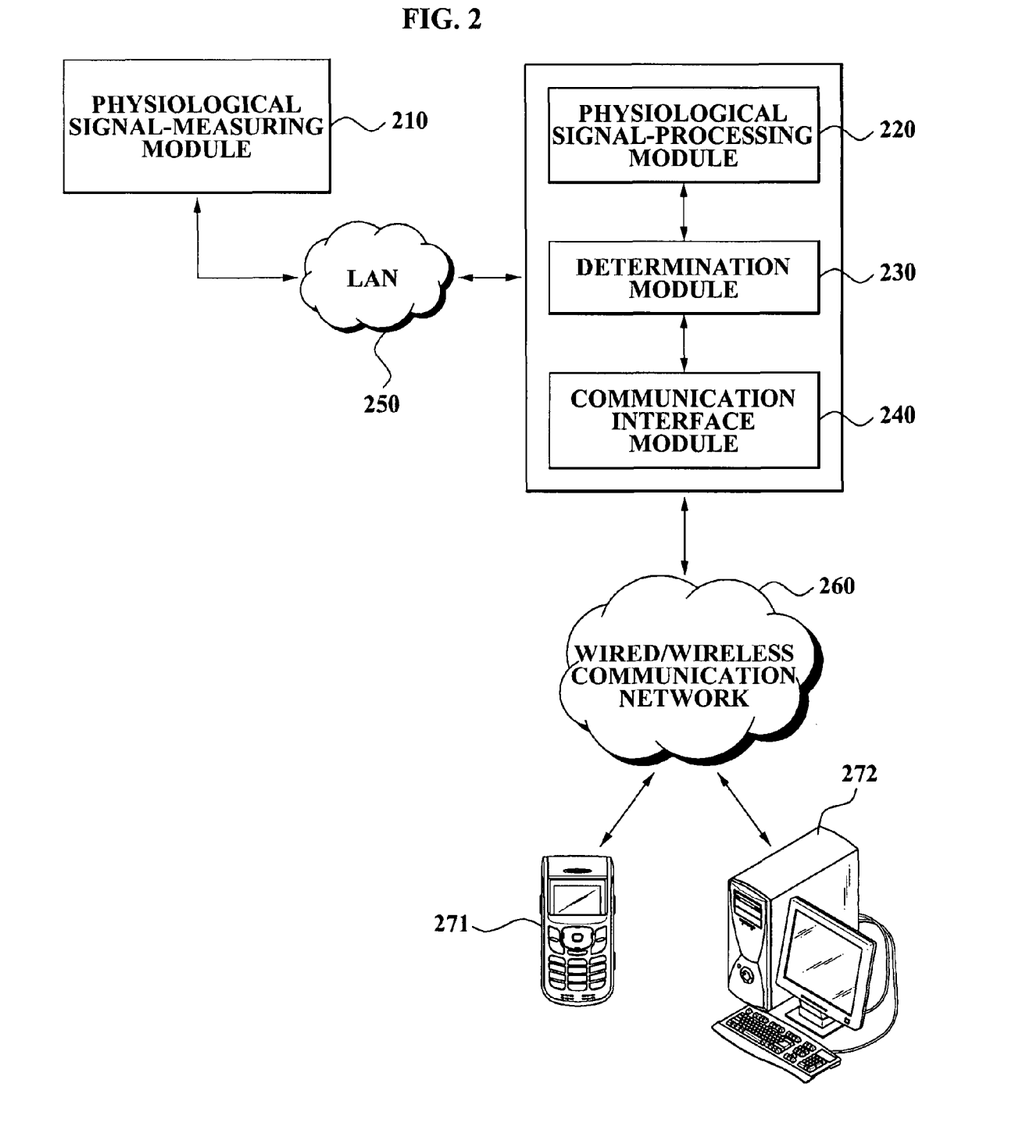
FIG. 2 is a block diagram illustrating the construction of an apparatus for sensing a sleeping condition of a user according to an embodiment of the present invention.

FIG. 2 is a block diagram illustrating the construction of an apparatus for sensing a sleeping condition of a user according to an embodiment of the present invention.

Referring to FIG. 2, the sleeping condition-sensing apparatus according to the present invention includes a physiological signal-measuring module 210, a physiological signal-processing module 220, a determination module 230, and a communication interface module 240.

The physiological signal-measuring module 210 serves to measure a physiological signal of a user who is sleeping. The physiological signal-measuring module 210 can electrically measure the physiological signal of the user through an electrode which is in close contact with a skin area over a soft body tissue of the user. The electrode includes a dry-type or wet-type electrode.

In addition, the physiological signal-measuring module 210 may measure the physiological signal of the user using an optical signal or a radio frequency (RF) signal. That is, as is well known in the art, the physiological signal-measuring module 210 may measure the physiological signal of the user through a signal transferring mechanism in which an optical or RF signal oscillated from the physiological signal-measuring module 210 is transmitted through the skin area and then is reflected or scattered from the body tissue below the skin area so as to be returned to the physiological signal-measuring module 210.

According to one embodiment of the present invention, the physiological signal-measuring module 210 may be implemented to have a construction independent of the physiological signal-processing module 220, the determination module 230 and the communication interface module 240. Namely, the physiological signal-measuring module 210 may be implemented to be interfaced with the sleeping condition-sensing apparatus including the physiological signal-processing module 220, the determination module 230 and the communication interface module 240 through a local area network (LAN) 250.

The physiological signal of the user measured through the physiological signal-measuring module 210 is transmitted to the physiological signal-processing module 220 through the LAN 250. In this case, the measured physiological signal may be partially or completely processed by the physiological signal-measuring module 210, or may be partially or completely processed by the physiological signal-processing module 220. In other words, an analog signal measured by the physiological signal-measuring module 210 may be wirelessly transmitted to the physiological signal-processing module 220 which in turn performs analog-to-digital conversion, filtering and various operations. Also, the physiological signal-measuring module 210 may perform analog-to-digital conversion, filtering and various operations on the analog physiological signal for transmission to the physiological signal-processing module 220.

The physiological signal-measuring module 210 transmits the measured physiological signal of the user to the communication interface module 240 through a LAN 250. The LAN 250 is a network including all wired/wireless local area communication networks. For the purpose of transmission of the physiological signal through the LAN 250, the physiological signal-measuring module 210 and the communication interface module 240 may be configured to include all local area communication modules for performing the local area communication according to Wireless LAN (WLAN), Bluetooth, Ultra Wide Band (UWB), Infrared Data Association (IrDA), Home Phoneline Networking Alliance (HPNA), Shared Wireless Access Protocol (SWAP) and IEEE 1394, etc.

The physiological signal-processing module 220 receives the measured physiological signal from the physiological signal-measuring module 210 through the communication interface module 240, and determines that the user moves into an awake state when a certain motion artifact is sensed from the received physiological signal. The case where an artifact signal is sensed from the measured physiological signal will be described hereinafter in detail with reference to FIG. 3.

Figure 3:
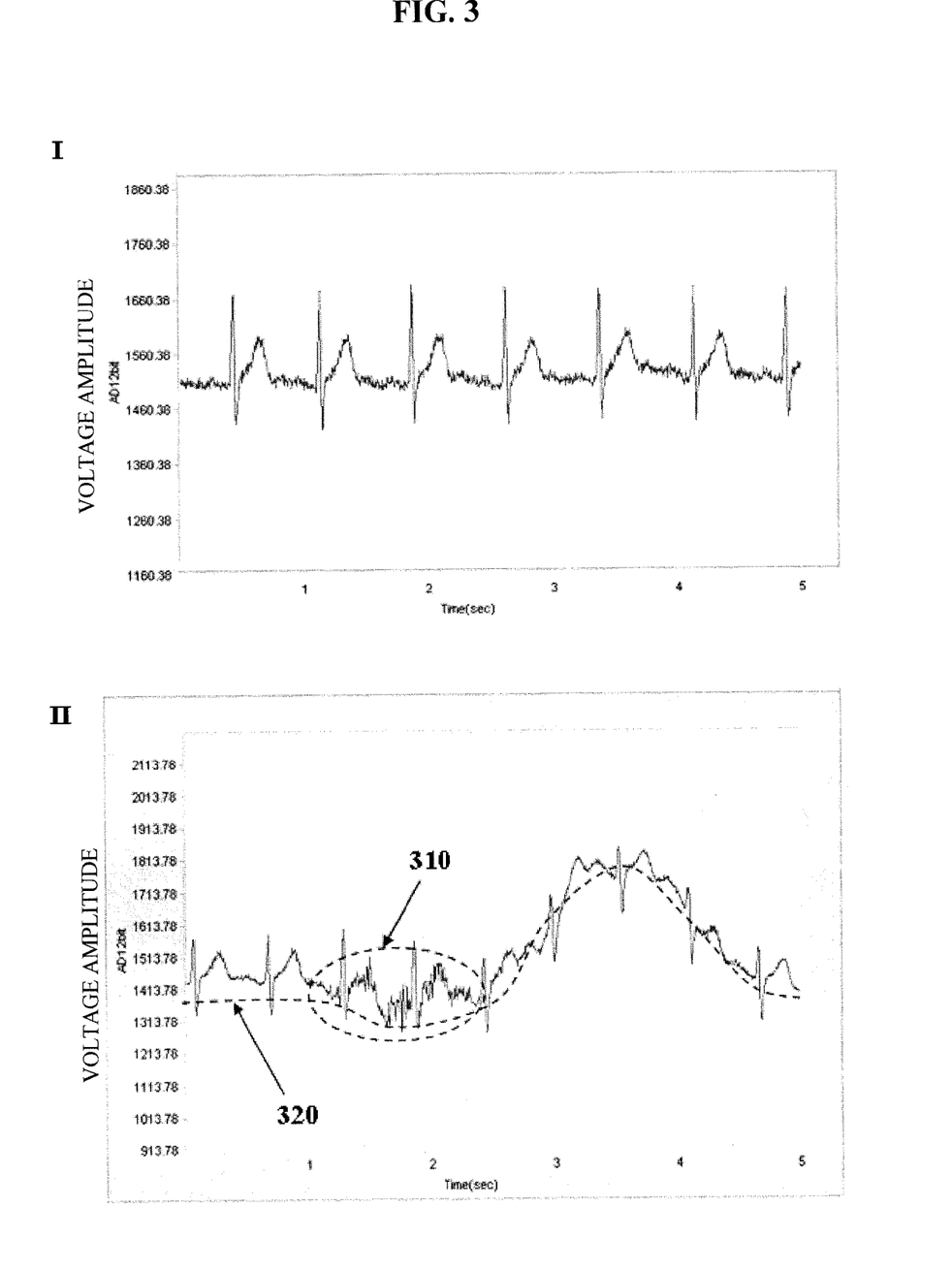
FIG. 3, parts I and II, are timing graphs illustrating waveforms of a physiological signal and a physiological signal containing a motion artifact according to an embodiment of the present invention.

FIG. 3, parts I and II, are timing graphs illustrating waveforms of a physiological signal and a physiological signal containing a motion artifact according to an embodiment of the present invention.

FIG. 3, part I, shows a graph of waveforms of a general physiological signal which can be measured from a user who is sleeping. As shown in part I of FIG. 3, a physiological signal having a regular magnitude and frequency can be measured from a user who is sleeping without any motion. However, when the user goes into an awake stage from the sleep stage such that a motion artifact is generated due to the user's tossing and turning, an artifact signal can be added to the physiological signal.

The artifact signal can be generated in a high-frequency component signal and a low-frequency component signal of the physiological signal, respectively. As shown in part II of FIG. 3, the artifact signal can be generated in the form of an irregular frequency 310 in the high-frequency component signal of the physiological signal. Also, the artifact signal can be generated in the form of an irregular magnitude 320 in the low-frequency component signal of the physiological signal.

This is because when a user moves into an awake stage, a motion artifact is generated due to his or her tossing and turning during sleep. For instance, when the motion artifact is generated, an EMG signal is generated due to the user's muscular motion, a noise is increased in the high-frequency component signal of the physiological signal due to the EMG signal. In addition, when the motion artifact is generated, the impedance between the skin and the electrode varies, and a drift may occur in which the magnitude of the physiological signal varies irregularly, i.e., the magnitude of the low-frequency component signal varies irregularly.

The increase in a noise of the high-frequency component signal and the drift of the low-frequency component signal due to a variation in the impedance can be sensed by the physiological signal-measuring module 210 based on the artifact signal of the physiological signal.

The sleeping condition-sensing apparatus according to the present invention can determine that a user moves into an awake stage when the artifact signal is generated in either a high-frequency component signal or a low-frequency component signal of the physiological signal, and when the artifact signal is generated in both a high-frequency component signal and a low-frequency component signal of the physiological signal.

A concrete method of sensing a motion artifact generated in a low-frequency component signal and a high-frequency component signal of the measured physiological signal will be described hereinafter in detail with reference to FIGS. 4 to 7.

Figure 4:
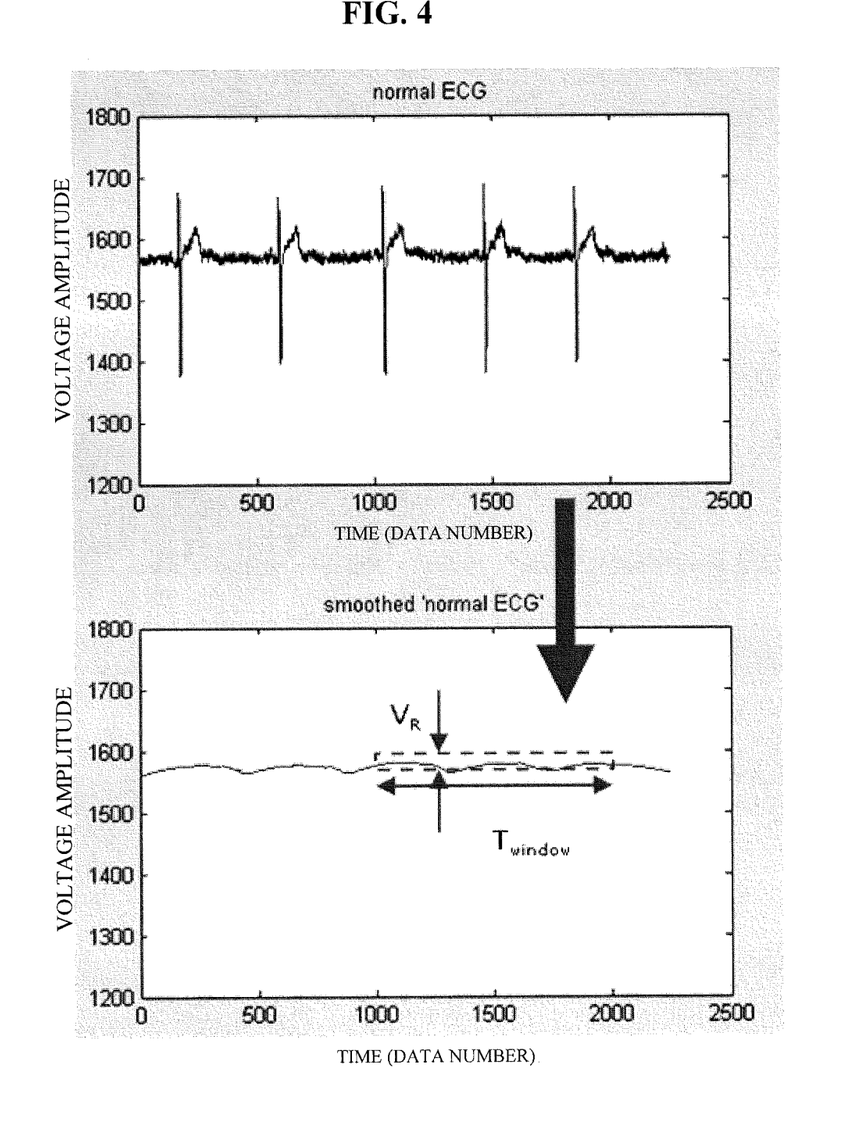
FIG. 4 is a graph illustrating a low frequency component signal extracted from a physiological signal of a user who is sleeping deeply according to an embodiment of the present invention.

FIG. 4 is a graph illustrating a low frequency component signal extracted from a physiological signal of a user who is sleeping deeply according to a preferred embodiment of the present invention.

Figure 5:
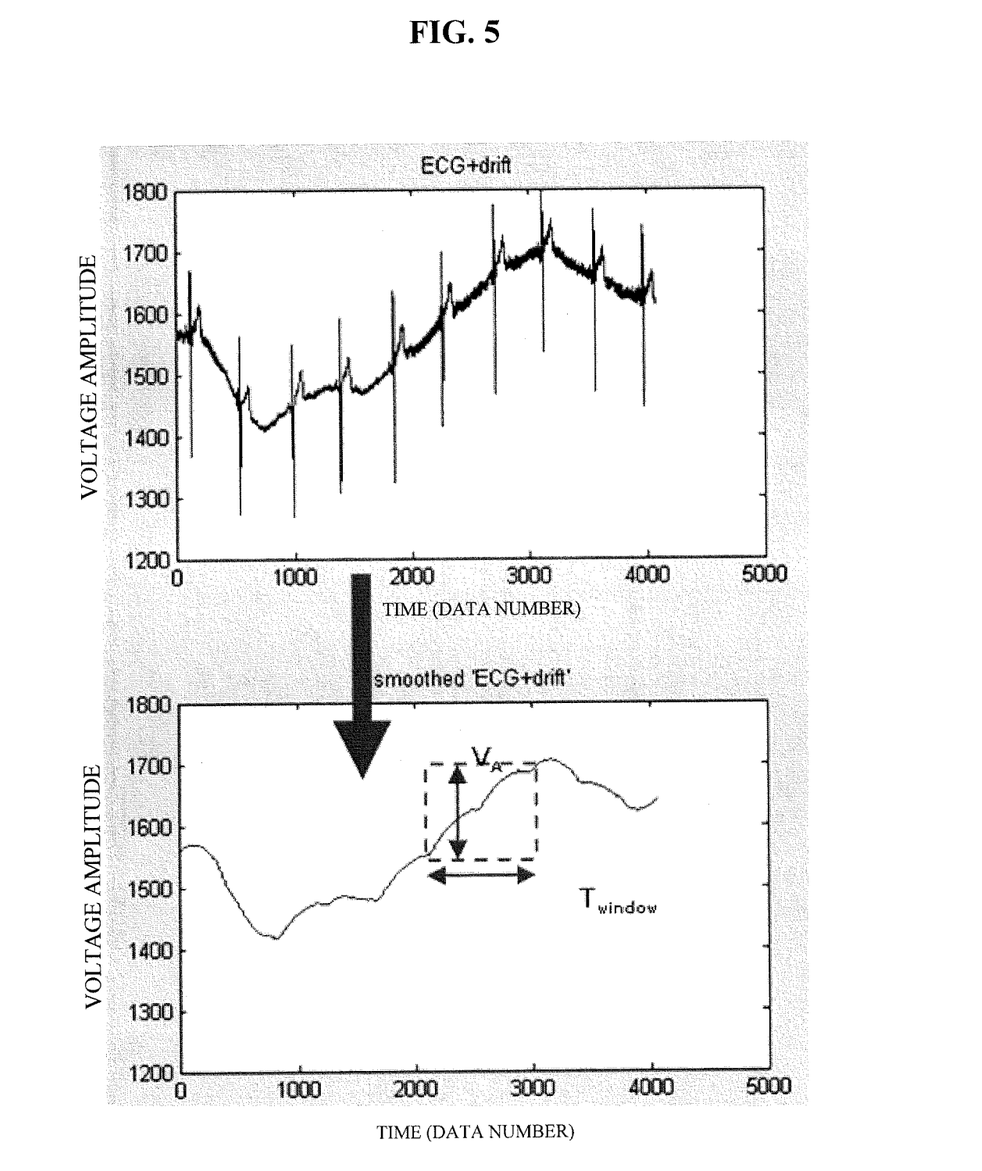
FIG. 5 is a graph illustrating a low frequency component signal extracted from a physiological signal of a user who moves into an awake state according to an embodiment of the present invention.

FIG. 5 is a graph illustrating a low frequency component signal extracted from a physiological signal of a user who moves into an awake state according to a preferred embodiment of the present invention.

According to one embodiment of the present invention, the determination of the sleeping condition of the user depends on whether or not there occurs a drift of the low-frequency component signal of the physiological signal of the user. A method of extracting the motion artifact from the measured physiological signal may employ various filtering methods, and as an example, the low-frequency component signal can be extracted from the measured physiological signal through the Savitzky-Lolay smoothing method.

According to one embodiment of the present invention, the physiological signal-processing module 220, as shown in FIGS. 4 and 5, can interpret the low-frequency component signal in terms of time domain. In the graphs of FIGS. 4 and 5, the abscissa denotes a time domain and the ordinate denotes a numerical value obtained by converting an analog value of a measured voltage into a digital value. Digit 1 of the abscissa means 4 ms.

The physiological signal-processing module 220 can determine whether or not a motion artifact is generated in the measured physiological signal using a difference between the maximum value and the minimum value of the low frequency component signal smoothed within a predetermined time interval of the abscissa. Specifically, when the difference between the maximum value and the minimum value is greater than a threshold value, it can be determined by the physiological signal-processing module 220 that the motion artifact is generated in the measured physiological signal.

For instance, as shown in FIGS. 4 and 5, the physiological signal-processing module 220 can calculate the maximum value and the minimum value of the low-frequency component signal within a $T_{window}$ interval of the time domain. The $T_{window}$ interval means 4 sec as falling within two scales of the abscissa, i.e., a time interval ranging from digits 1000 to digit 2000. At this time, assuming that the threshold value is 10 and the difference between the maximum value and the minimum value of the low-frequency component signal is calculated as 5 in the $T_{window}$ interval, the physiological signal-processing module 220 determines that the motion artifact is not contained in the measured physiological signal and the determination module 230 determines that the user maintains the sleep stage in the $T_{window}$ interval accordingly.

However, as shown in FIG. 5, when the difference between the maximum value and the minimum value of the low-frequency component signal is calculated as 100 in the $T_{window}$ interval, the physiological signal-processing module 220 determines that the motion artifact is contained in the measured physiological signal and the determination module 230 determines that the user moves into the awake stage in the $T_{window}$ interval accordingly.

As such, the physiological signal-processing module 220 determines whether or not the difference between the maximum value and the minimum value of the low-frequency component signal is greater than the threshold value within a predetermined time interval to sense whether or not there occurs a drift of the low-frequency component signal. When the physiological signal-processing module 220 senses that the drift occurs, the determination module 230 can determine that the user goes into the awake stage from the sleep stage within the predetermined time interval. Such determination of whether or not there occurs the drift of the low-frequency component signal by the physiological signal-processing module 220 can be performed in the entire time interval during all the sleep stages of the user.

As described above, the physiological signal-processing module 220 determines whether or not the motion artifact is contained in the measured physiological signal of the user using the difference between the maximum value and the minimum value of the low-frequency component signal of the measured physiological signal within a predetermined time interval, and the determination module 230 may determine whether or not the user goes into the awake stage from the sleep stage within the predetermined interval based on a determination result or may determine whether or not a gradient of the low-frequency component signal is greater than a predetermined threshold value to check whether or not the user goes into the awake stage from the sleep stage within the predetermined time interval.

For instance, in FIGS. 4 and 5, the physiological signal-processing module 220 can calculate a gradient of the low-frequency component signal, respectively. A method of calculating the gradient of the low-frequency component signal may adopt various kinds of any of the methods of calculating a gradient of graphs. For instance, a gradient of a straight line formed by connecting a starting point and an ending point of the $T_{window}$ interval may be set as an index, and a gradient of a straight line formed by connecting two points on the abscissa in the $T_{window}$ interval or a gradient of a straight line obtained by finding all the data using the least mean square (LMS) method may be set as an index.

In this case, assuming that the threshold value is 1 and the gradient of the low-frequency component signal is calculated as 0.1, the determination module 130 can determine that the user maintains the sleep stage in the $T_{window}$ interval.

However, as shown in FIG. 5, when the gradient of the low-frequency component signal is calculated as 1.5, the determination module 130 can determine that the user moves into the awake stage from the sleep stage in the $T_{window}$ interval.

Respective threshold values depending on the above-mentioned two cases, i.e., a threshold value depending on a case of using a difference between the maximum value and the minimum value of the low-frequency component signal, and a threshold value depending on a case of using a gradient of the straight line, may be fixed values determined by a person of ordinary skill in the art and may be various stage values or variable values. Particularly, the two threshold values may be set to have different values depending on the determination of a person of ordinary skill in the art in view of the bodily characteristics of the user depending upon circumstances.

A method of interpreting the low-frequency component signal of the measured physiological signal of the user based on the time domain graphs in FIGS. 4 and 5 has been described hereto.

An explanation on a method of interpreting the measured physiological signal on the frequency domain according to another embodiment of the present invention will be given hereinafter with reference to FIGS. 6 and 7.

Figure 6:
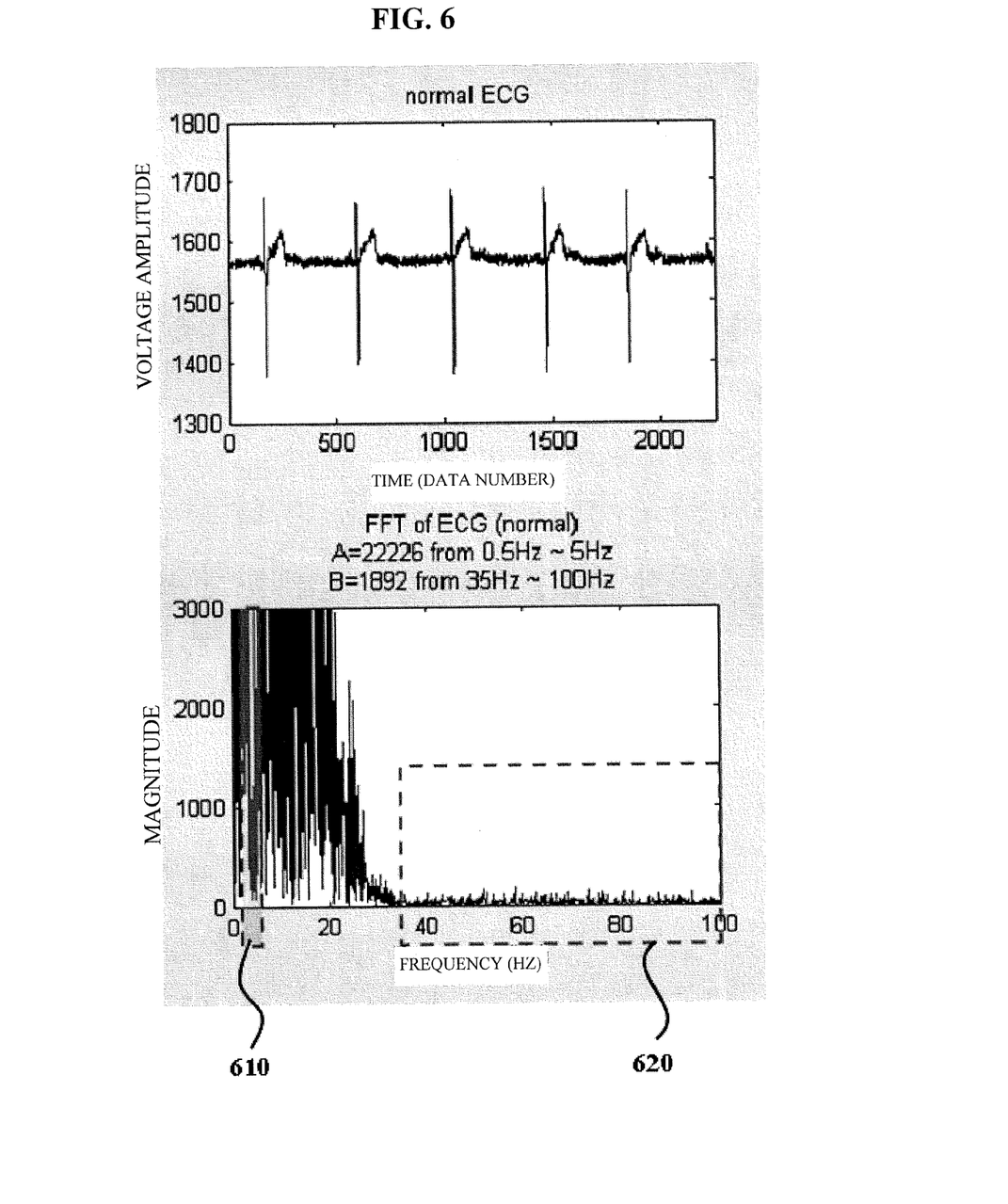
FIG. 6 is a graph illustrating transformation of a physiological signal of a user who is sleeping deeply, into a frequency domain form, according to an embodiment of the present invention.
Figure 7:
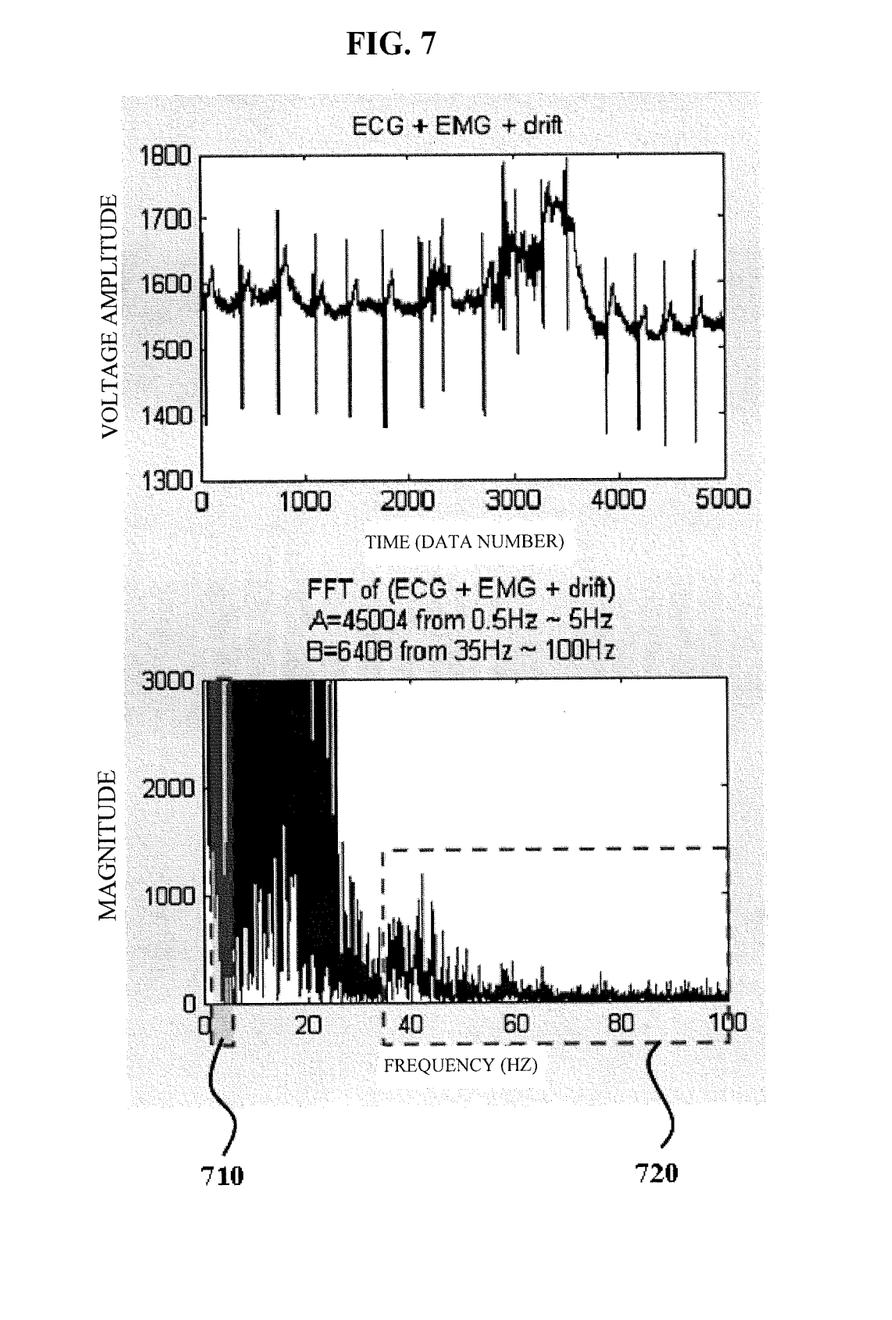
FIG. 7 is a graph illustrating transformation of a physiological signal of a user who moves into an awake state, into a frequency domain form, according to an embodiment of the present invention.

FIG. 6 is a graph illustrating transformation of a physiological signal of a user who is sleeping deeply, into a frequency domain form, according to a preferred embodiment of the present invention, and FIG. 7 is a graph illustrating transformation of a physiological signal of a user who moves into an awake state, into a frequency domain form, according to a preferred embodiment of the present invention.

According to another embodiment of the present invention, the physiological signal-processing module 220 receives the measured physiological signal of the user from the physiological signal-measuring module 220 and interprets the received physiological signal through a graph having a frequency domain. For example, a physiological signal graph on the time domain shown in the upper sides of the FIGS. 6 and 7 can be subjected to a fast Fourier transform (FFT) so as to be transformed into a physiological signal graph having a frequency domain shown in the lower portions of FIGS. 6 and 7.

As such, whether or not there is generated an artifact or a noise in the physiological signal graph can be sensed by calculating a power of the physiological signal in respective frequency bands. The power of the physiological signal can be obtained by calculating the area of the physiological signal in each frequency band in the frequency domain graph.

As mentioned above, the physiological signal-measuring module 220 can sense a noise for a low-frequency component signal and a high-frequency component signal of the measured physiological signal. In the case where the user moves into an awake stage from the sleep stage to thereby generate a motion artifact, as described above through FIG. 3, a drift occurs in the low-frequency component signal and a noise having an irregular frequency is generated in the high-frequency component signal. Thus, in the case where the motion artifact is contained in the measured physiological signal, all the signals of respective frequency bands are increased in power. The sleeping condition-sensing apparatus according to another embodiment of the present invention can sense whether or not the motion artifact is contained in the measured physiological signal through analysis of the frequency domain using the above principle.

More specifically, for example, a frequency band 610 of a low-frequency component signal ranges from 0.5 to 5 Hz, and a frequency band 620 of a high-frequency component signal ranges from 35 to 100 Hz in FIG. 6. Assuming that a power threshold value of the low-frequency component signal is 30,000 and a power threshold value of the high-frequency component signal is 3,000, when the power value in each frequency band is greater than the each power threshold value, it can be determined that the user moves into an awake stage from the sleep stage in FIG. 6.

When a power value (area) in the frequency band 610 of the low-frequency component signal is calculated as 22,226 and a power value (area) in the frequency band 620 of the high-frequency component signal is calculated as 1,892 in FIG. 6, the respective power values are smaller than the respective power threshold values 30,000 and 3,000 and hence the determination module 230 determines that the user maintains the sleep stage.

As such, the physiological signal-processing module 220 can determine that the motion artifact is contained in the measured physiological signal only when the power values in the respective frequency bands are greater than the respective power threshold values. Also, when any one of the respective power values in the respective frequency bands is greater than the corresponding power threshold value, the physiological signal-processing module 220 can determine that the motion artifact is contained in the measured physiological signal. The determination of the sleeping condition may be implemented in various methods by a person of ordinary skill in the art.

As shown in FIG. 6, the power values in the respective frequency bands can be measured as being smaller than the respective power threshold values in the sleep stage of the user, but can be measured as being greater than the respective power threshold values in the awake stage of the user as shown in FIG. 7. As shown in FIG. 7, in the case of transforming the physiological signal measured in the awake stage of the user into the frequency domain graph, the respective frequency band signals have a value greater than that of the respective frequency band signals in the graph shown in FIG. 6.

Similar to the case of FIG. 6, a frequency band 710 of a low-frequency component signal ranges from 0.5 to 5 Hz, and a frequency band 720 of a high-frequency component signal ranges from 35 to 100 Hz in FIG. 7. Assuming that a power threshold value of the low-frequency component signal is 30,000 and a power threshold value of the high-frequency component signal is 3,000, when the power value in each frequency band is greater than each power threshold value, it can be determined that the user moves into an awake stage from the sleep stage.

When a power value (area) in the frequency band 710 of the low-frequency component signal is calculated as 45,004 and a power value (area) in the frequency band 720 of the high-frequency component signal is calculated as 6,408 in FIG. 7, the respective power values are greater than the respective power threshold values 30,000 and 3,000 and hence the determination module 230 determines that the user moves into the awake stage from the sleep stage.

As such, the physiological signal-measuring module 220 can determine that the motion artifact is contained in the measured physiological signal only when the power values in the respective frequency bands are greater than the respective power threshold values. Also, when any one of the respective power values in the respective frequency bands is greater than the corresponding power threshold value, the physiological signal-processing module 220 can determine that the motion artifact is contained in the measured physiological signal. The determination of the sleeping condition may be implemented in various methods by a person of ordinary skill in the art.

The communication interface module 240 can transmit determination result data including information on the frequency of awakenings during sleep, i.e., the frequency of the user's failings into the awake stage determined by the determination module 230 by means of the above-mentioned various methods, to a predetermined remote device including a cellular phone 271 or a personal computer (PC) 272 through a wired/wireless communication network 260. That is, the sleeping condition-sensing apparatus according to the present invention can be implemented so that it performs only the operation of calculating the result data including information on the frequency of awakenings during sleep depending on whether or not the motion artifact is contained in the measured physiological signal of the user, and the determination of the sleeping condition of the user is performed by the remote device connected to the communication interface module 240 through the wired/wireless communication network 260.

As described above, according to the sleeping condition-sensing apparatus of the present invention, whether a sleeping user sleeps deeply or moves into an awake stage from the sleep stage can be determined only through detection of a motion artifact from the measured physiological signal of the user. In addition, in the case where the frequency of awakenings of the user is detected to be abnormally high during the entire sleep period, the inventive sleeping condition-sensing apparatus may inform the user of a symptom of sleep disorders through a display means or a sound output means.

Moreover, the inventive sleeping condition-sensing apparatus can detect the sleeping user's falling into the awake stage to control the reproduction time of an alarm signal. That is, in the case where it is sensed that the user goes into an awake stage from the sleep stage within a predetermined time (for example, within 30 minutes) before an alarm time preset by the user, the sleeping condition-sensing apparatus can reproduce an alarm signal immediately. In this case, the user has an advantageous effect that he or she can awake early and more refreshed than awake from a shallow sleep stage.

Further, the sleeping condition-sensing apparatus of the present invention can predict a next sleep cycle based on a function of sensing the user's falling into an awake stage during sleep. The sleep stages during sleep forms a kind of cycle having recurring patterns. Initially, in the case of a first cycle, the user passes through an awake stage, a shallow-sleep stage (including sleep stages 1 and 2), a deep-sleep stage (including sleep stages 3 and 4), the shallow-sleep stage, a rapid eye movement (REM) stage, and the awake stage to form one cycle. It is known that approximately 90 minutes are typically spent during the initial cycle. A cycle whose period is short recurs, and the deep-sleep phase disappears over time. From the view point of such typical tendency of sleep stages, when the measured time interval of the awake stage is extracted to analyze the sleeping condition, it is possible to predict when the user will fall into a next awake stage.

If the sleeping data of the user recorded at night are individually or collectively stored in a database, more useful information can be extracted therefrom. For example, in the case of constructing a database for the typical awake pattern during sleep, it can be expected that a symptom of paroxysmal sleep, restless legs syndrome (RLS), somnambulism, etc., would be inferred.

Figure 8:
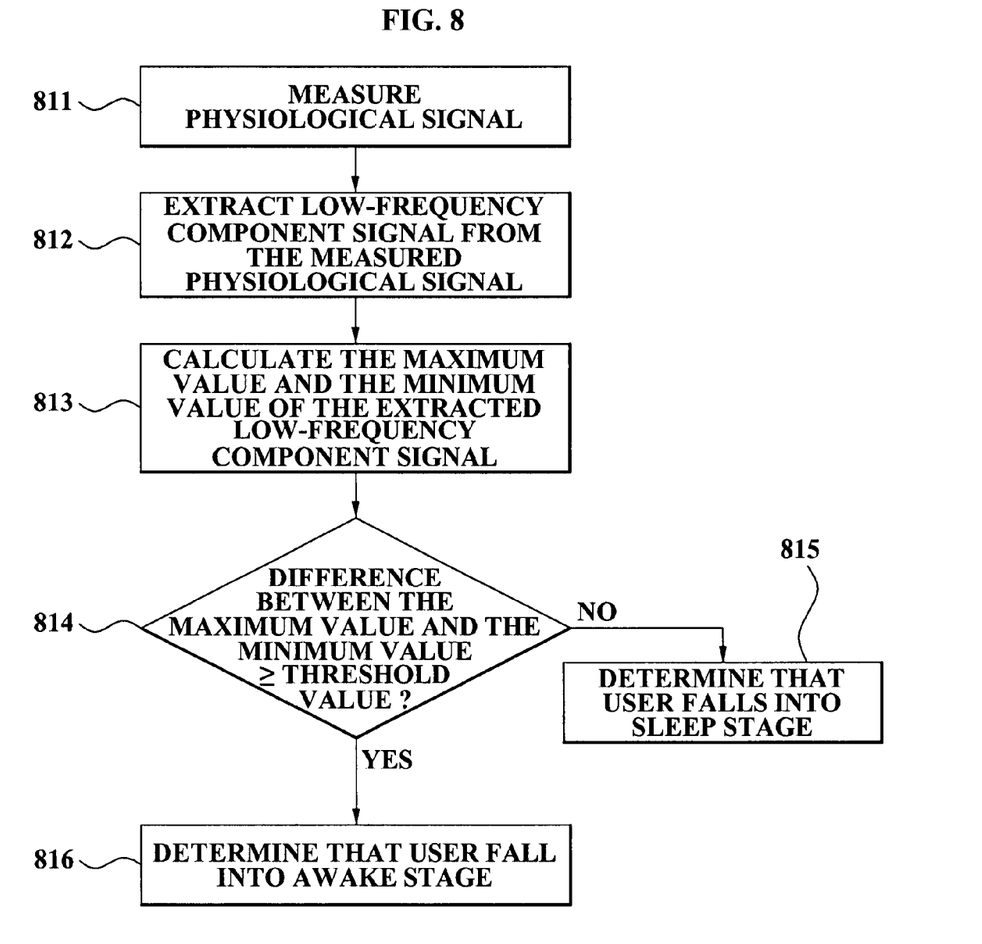
FIG. 8 is a flowchart illustrating the process of sensing a sleeping condition of a user using a difference between the maximum value and the minimum value of a low frequency component signal extracted from a physiological signal of a user according to an embodiment of the present invention.

FIG. 8 is a flowchart illustrating the process of sensing a sleeping condition of a user using a difference between the maximum value and the minimum value of a low frequency component signal extracted from a physiological signal of a user according to a preferred embodiment of the present invention.

Referring to FIG. 8, the sleeping condition-sensing apparatus according to one embodiment of the present invention measures a physiological signal of a user who is sleeping in operation 811. The sleeping condition-sensing apparatus extracts a low-frequency component signal from the measured physiological signal in operation 812. Then, the sleeping condition-sensing apparatus calculates the maximum value and the minimum value of the extracted low-frequency component signal within a predetermined time interval in operation 813. Subsequently, in operation 814, the sleeping condition-sensing apparatus determines whether or not a difference between the maximum value and the minimum value is greater than a predetermined threshold value. When it is determined in operation 814 that the difference between the maximum value and the minimum value is less than the predetermined threshold value, the program proceeds to operation 815 where the sleeping condition-sensing apparatus determines that the user maintains a sleep stage within the predetermined time interval. Conversely, when it is determined in operation 814 that the difference between the maximum value and the minimum value is greater than the predetermined threshold value, the program proceeds to operation 816 where the sleeping condition-sensing apparatus determines that the user moves into an awake stage within the predetermined time interval.

Figure 9:
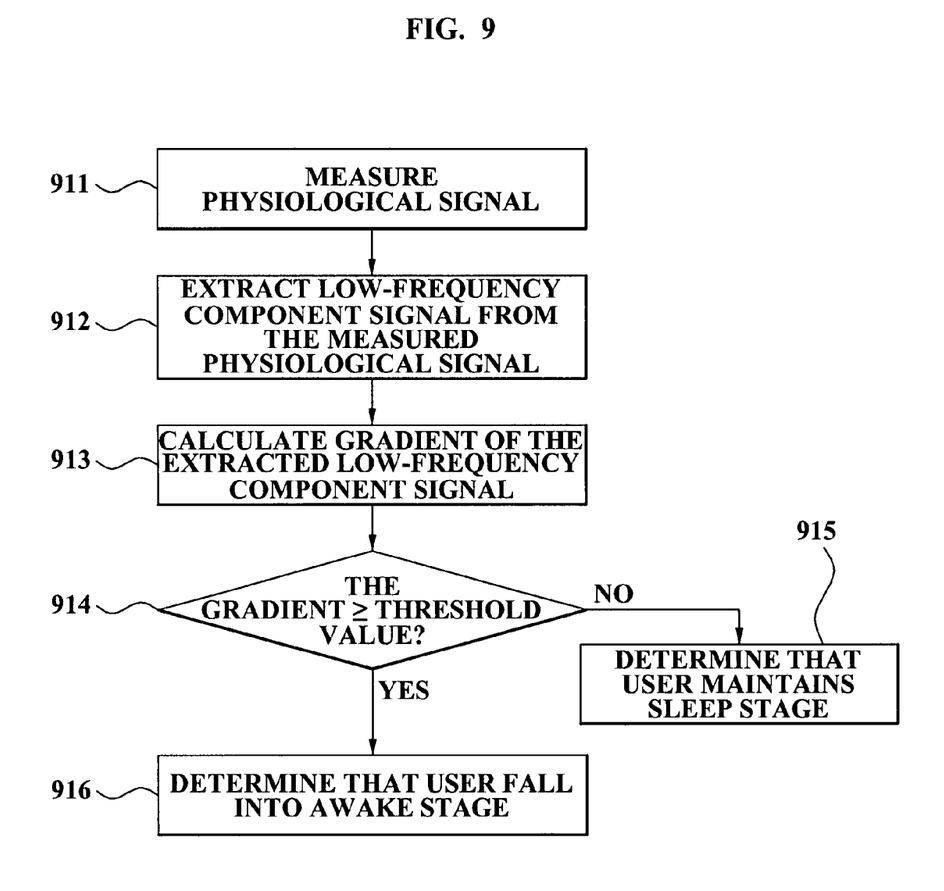
FIG. 9 is a flowchart illustrating the process of sensing a sleeping condition of a user using a gradient of a low frequency component signal extracted from a physiological signal of a user according to an embodiment of the present invention.

FIG. 9 is a flowchart illustrating the process of sensing a sleeping condition of a user using a gradient of a low frequency component signal extracted from a physiological signal of a user according to a preferred embodiment of the present invention.

Referring to FIG. 9, the sleeping condition-sensing apparatus according to one embodiment of the present invention measures a physiological signal of a user who is sleeping in operation 911. The sleeping condition-sensing apparatus extracts a low-frequency component signal from the measured physiological signal in operation 912. Then, the sleeping condition-sensing apparatus calculates a gradient of the extracted low-frequency component signal within a predetermined time interval in operation 913. Subsequently, in operation 914, the sleeping condition-sensing apparatus determines whether or not the gradient of the low-frequency component signal is greater than a predetermined threshold value. When it is determined in operation 914 that the gradient is less than the predetermined threshold value, the program proceeds to operation 915 where the sleeping condition-sensing apparatus determines that the user maintains a sleep stage for the predetermined time interval. Conversely, when it is determined in operation 914 that the gradient is greater than the predetermined threshold value, the program proceeds to operation 916 where the sleeping condition-sensing apparatus determines that the user moves into an awake stage within the predetermined time interval.

Figure 10:
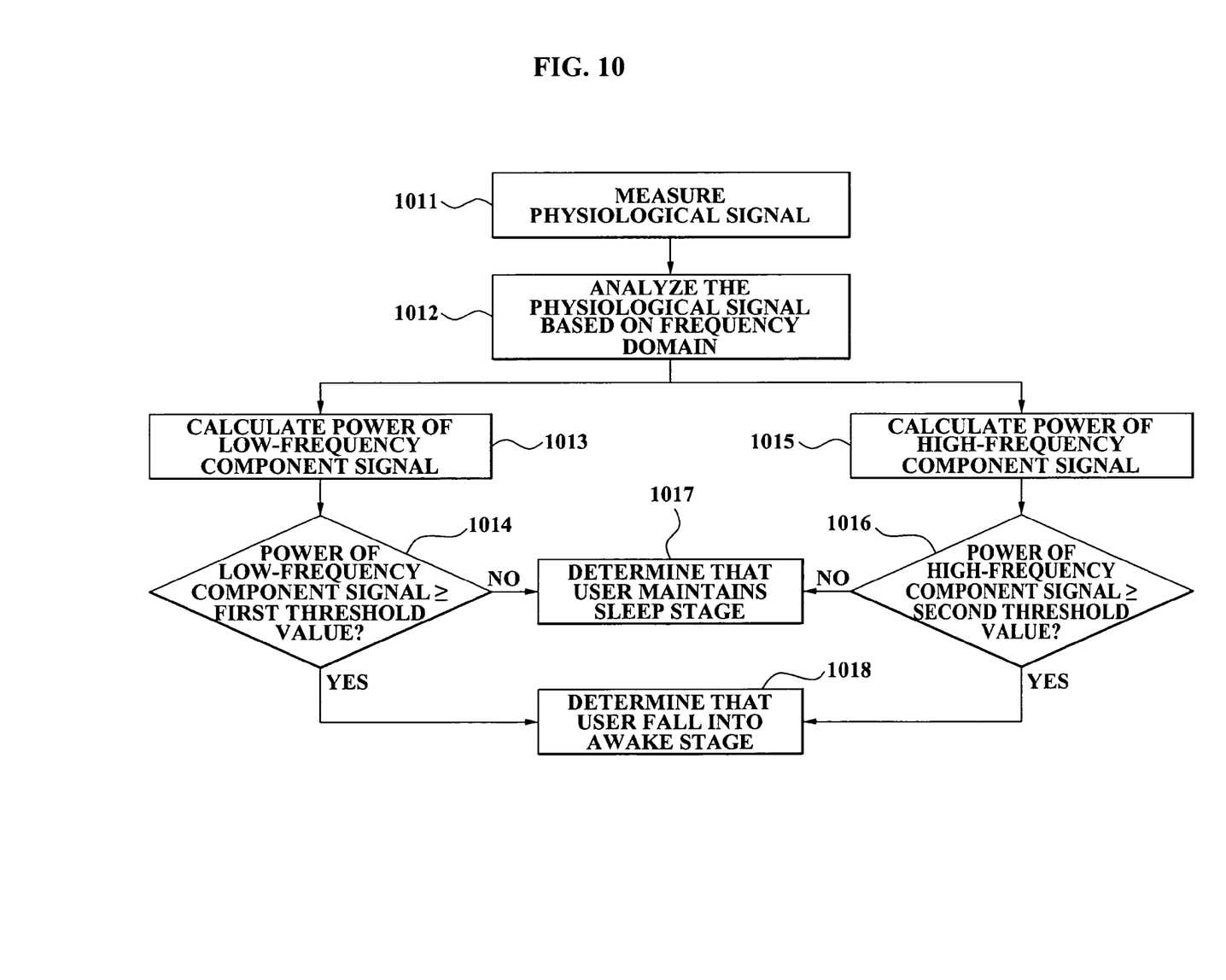
FIG. 10 is a flowchart illustrating the process of sensing a sleeping condition of a user based on analysis of a frequency domain of a physiological signal of a user according to an embodiment of the present invention.

FIG. 10 is a flowchart illustrating the process of sensing a sleeping condition of a user based on analysis of a frequency domain of a physiological signal of a user according to an embodiment of the present invention.

Referring to FIG. 10, the sleeping condition-sensing apparatus according to one embodiment of the present invention measures a physiological signal of a user who is sleeping in operation 1011. The sleeping condition-sensing apparatus transforms the physiological signal graph measured based on the time domain into a physiological signal graph having the frequency domain, and then analyzes the transformed physiological signal in operation 1102. The sleeping condition-sensing apparatus calculates a power of a low-frequency component signal of the measured physiological signal corresponding to a predetermined time interval on the frequency domain graph in operation 1013. In a next operation 1014, the sleeping condition-sensing apparatus determines whether or not the power of the low-frequency component signal is greater than a first threshold value. When it is determined in operation 1014 that the power of the low-frequency component signal is smaller than the first threshold value, the program proceeds to operation 1017 where the sleeping condition-sensing apparatus determines that the user maintains a sleep stage within the predetermined time interval. Conversely, when it is determined in operation 1014 that the power of the low-frequency component signal is greater than the first threshold value, the program proceeds to operation 1018 where the sleeping condition-sensing apparatus determines that the user moves into an awake stage within the predetermined time interval.

In addition, the sleeping condition-sensing apparatus calculates a power of a high-frequency component signal of the measured physiological signal corresponding to a predetermined time interval on the frequency domain graph in operation 1015. In a next operation 1016, the sleeping condition-sensing apparatus determines whether or not the power of the high-frequency component signal is greater than a second threshold value. When it is determined in operation 1016 that the power of the high-frequency component signal is smaller than the second threshold value, the program proceeds to operation 1017 where the sleeping condition-sensing apparatus determines that the user maintains a sleep stage for the predetermined time interval. Conversely, when it is determined in operation 1016 that the power of the high-frequency component signal is greater than the second threshold value, the program proceeds to operation 1018 where the sleeping condition-sensing apparatus determines that the user moves into an awake stage within the predetermined time interval.

At this time, the sleeping condition-sensing apparatus may determine that the user moves into the awake stage when both the power of the low-frequency component signal and the power of the high-frequency component signal are greater than the first and second threshold values, respectively, or when any one of the powers of the low-frequency component signal and the high-frequency component signal is greater than the corresponding first or second threshold value.

Although the present invention has been described briefly, the sleeping condition-sensing method according to the present invention described with reference to FIGS. 8 to 10 may be implemented while covering the sleeping condition-sensing operation of the inventive sleeping condition-sensing apparatus described with reference to FIGS. 2 to 7.

In addition, the sleeping condition-sensing method according to the present invention may be implemented in the form of a program command executable through various computers, and recorded in a computer-readable recording medium. The computer-readable recording medium may include program commands, data files, data structures, or the like alone or a combination thereof. The program commands of the computer-readable recording medium may be ones designed and configured specially for the sake of the present invention, or ones that are well-known to and can be used by those skilled in the computer software field. Examples of the computer-readable recording medium include magnetic media such as hard disks, floppy disks and magnetic tapes, optical media such as CD-ROMs, DVD, etc., magneto-optical media such as optical disks, and hardware devices such as ROMs, RAMs, flash memories, etc., that are configured specially to store and execute program commands. Also, the computer-readable recording medium may include transmission media of light or metal wires, wave guides, etc., including carrier waves that transmit a signal for designating the program commands, data structures, etc. Examples of the program commands include machine language codes as construed by a compiler as well as high-level language codes executable by a computer using interpreters, etc. The hardware devices may be configured to be operated as at least one software module to perform the operation of the present invention, and vice-versa.

According to the sleeping condition-sensing apparatus and method of the present invention, it is possible to obtain an advantageous effect that it can be determined that a sleeping user moves into an awake state when a certain motion artifact is sensed from his or her physiological signal being measured, so that the quality of sleep can be determined based on only an artifact signal generated during the measurement of the physiological signal of the user without an additional physiological signal measuring instrument.

In addition, according to the sleeping condition-sensing apparatus and method of the present invention, it is also possible to obtain an advantageous effect that a sleeping user's falling into an awake stage can be sensed and predicted through a motion artifact generated from a physiological signal of the user so as to provide an alarm to him or her within an alarm time range preset by the user so that he or she can optimize the time to get up, i.e., an awake time.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method of sensing a sleeping condition of a body, the method comprising:
   detecting a physiological signal of a body using a physiological signal measuring module;
   detecting a predetermined motion artifact that identifies movement of the body from the detected physiological signal;
   determining, using at least one processing device, whether the body has gone into an awake state based on the predetermined motion artifact being detected in the detected physiological signal; and
   predicting a next awake state based on a time interval of the determined awake state during a period of sleep,
   wherein the physiological signal is an electrocardiogram (ECG).

2. The method of claim 1, wherein the detecting of the physiological signal comprises electrically detecting the physiological signal of the body through a dry or wet type electrode which is in close contact with a skin area over a soft body tissue of the body.

3. The method of claim 1, wherein the detecting of the physiological signal comprises detecting the physiological signal of the body using an optical or radio frequency signal.

4. The method of claim 1, wherein the physiological signal comprises an electrocardiogram (ECG) signal, a photoplethysmogram (PPG) signal, or a galvanic skin response (GSR) signal.

5. The method of claim 1, wherein the detected predetermined motion artifact in the detected physiological signal, identifying the movement of the body, comprises a drift indicator of a low-frequency component signal of the detected physiological signal.

6. A method of sensing a sleeping condition of a user, the method comprising:
   measuring a physiological signal of a user who is sleeping using a physiological signal measuring module;
   determining, using at least one processing device, whether or not a predetermined motion artifact is contained in the measured physiological signal, including extracting a low-frequency component signal from the measured physiological signal, calculating the maximum value and the minimum value of the extracted low-frequency component signal within a predetermined time interval, and determining that the motion artifact is contained in the measured physiological signal within the predetermined time interval when a difference between the maximum value and the minimum value is greater than a predetermined threshold value;
   determining that the user always goes into an awake state when the predetermined motion artifact is contained in the measured physiological signal; and
   predicting a next awake state based on a time interval of the determined awake state during a period of sleep,
   wherein the physiological signal is an electrocardiogram (ECG).

7. The method of claim 5, wherein the determining further comprises:

extracting the low-frequency component signal from the measured physiological signal;

calculating a respective gradient of the extracted low-frequency component signal within each of predetermined time intervals; and determining the awake state when a respective motion artifact is contained in the measured physiological signal within the respective predetermined time intervals when the respective gradient is greater than a predetermined threshold value.

8. The method of claim 5, wherein the determining further comprises:

calculating a respective power of the low-frequency component signal corresponding to each of plural same predetermined time intervals; and determining that a respective motion artifact is contained in the detected physiological signal within the respective predetermined time intervals when the respective power of the low-frequency component signal is greater than a first predetermined threshold value.

9. The method of claim 1, wherein the predetermined motion artifact comprises high-frequency noise of the detected physiological signal.

10. The method of claim 9, wherein the determining further comprises:

calculating a respective power of the high-frequency noise corresponding to each of plural same predetermined time intervals; and determining that the motion artifact is contained in the detected physiological signal within respective predetermined time intervals when the respective power of the high-frequency noise is greater than a predetermined threshold value.

11. A non-transitory computer-readable recording medium storing a program used to implement the method of any one of claims 1 to 10.

12. An apparatus for sensing a sleeping condition of a body, comprising:

a physiological signal-detecting module configured to detect a physiological signal of a body using a physiological signal measuring module;

a physiological signal-processing module configured to detect a predetermined motion artifact that identifies movement of the body from the detected physiological signal; and a determination module configured to determine whether the body has gone into an awake state based on the predetermined motion artifact being detected in the detected physiological signal, wherein a next awake state is predicted based on a time interval of the determined awake state during a period of sleep, and wherein the physiological signal is an electrocardiogram (ECG).

13. The apparatus of claim 12, wherein the physiological signal-detecting module electrically detects the physiological signal of the body through a dry or wet type electrode which is in close contact with a skin area over a soft body tissue of the body.

14. The apparatus of claim 12, wherein the physiological signal-detecting module detects the physiological signal of the body using an optical or radio frequency signal.

15. The apparatus of claim 12, wherein the detected predetermined motion artifact in the detected physiological signal, identifying movement of the body, comprises a drift indicator of a low-frequency component signal of the detected physiological signal.

16. The apparatus of claim 12, wherein the predetermined motion artifact comprises high-frequency noise of the detected physiological signal.

17. The apparatus of claim 12 further comprising a communication interface module for transmitting determination result data including information on a frequency of awakenings during sleep, represented by one or more detected predetermined motion artifacts, to a predetermined remote device through a wired/wireless communication network, wherein the frequency of awakenings during sleep includes a frequency of the body's moving into the awake state determined by the determination module.

18. The apparatus of claim 17, wherein the communication interface module is configured to transmit the determination result data to a cellular phone.

19. The apparatus of claim 17, wherein the communication interface module is configured to transmit the determination result data to a personal computer.

20. The method of claim 1, wherein the physiological signal indicates respective plural different sleep states, including the awake state, over multiple predetermined time intervals based on respective results of the determining of whether the body has fallen into the awake state, including corresponding results indicating that the body has not fallen into the awake state.

21. The method of claim 5, wherein the determining further comprises:

extracting the low-frequency component signal from the measured physiological signal;

calculating the maximum value and the minimum value of the extracted low-frequency component signal within a predetermined time interval; and determining that the motion artifact is contained in the measured physiological signal within the predetermined time interval when a difference between the maximum value and the minimum value is greater than a predetermined threshold value.

22. The method of claim 1, further comprising predicting a next sleep cycle based on a function of the detected awake state.

23. The method of claim 8, wherein the determining further comprises:

calculating a respective power of the high-frequency noise corresponding to each of plural same predetermined time intervals; and determining that the motion artifact is contained in the detected physiological signal within respective predetermined time intervals when at least one of the respective power of the high-frequency noise is greater than a second predetermined threshold value and the respective power of the low-frequency noise is greater than the first predetermined threshold value.

24. The method of claim 1, wherein the predetermined motion artifact is a low-frequency drift detected in the physiological signal, such that the low-frequency drift exceeds a predetermined threshold gradient value.

25. The method of claim 6, wherein the predetermined motion artifact comprises a drift of the low-frequency component signal of the physiological signal.

26. The apparatus of claim 12, wherein the predetermined motion artifact is a low-frequency drift in the physiological signal, such that the low-frequency drift exceeds a predetermined threshold gradient value.

* * * * *